(12) United States Patent  (10) Patent No.: US 9,023,042 B1
Huron  (45) Date of Patent: May 5, 2015

(54) BIPOLAR ELECTROSURGICAL COAGULATOR

(76) Inventor: Keith Huron, Jacksonville, FL (US)

( * ) Notice: Subject to any disclaimer, the term of this patent is extended or adjusted under 35 U.S.C. 154(b) by 1242 days.

(21) Appl. No.: 12/878,189

(22) Filed: Sep. 9, 2010

Related U.S. Application Data

(60) Provisional application No. 61/240,862, filed on Sep. 9, 2009.

(51) Int. Cl.
    *A61B 18/18* (2006.01)
    *A61B 18/00* (2006.01)

(52) U.S. Cl.
    CPC ....... *A61B 18/00* (2013.01); *A61B 2018/00589* (2013.01); *A61B 2018/00321* (2013.01)

(58) Field of Classification Search
    CPC ............ A61B 2018/00589; A61B 2018/00321
    USPC ................................................ 606/40, 49, 50
    See application file for complete search history.

(56) References Cited

U.S. PATENT DOCUMENTS

| | | | | |
|---|---|---|---|---|
| 1,983,669 A | * | 12/1934 | Kimble | 606/50 |
| 3,801,766 A | * | 4/1974 | Morrison, Jr. | 200/553 |
| 4,476,862 A | * | 10/1984 | Pao | 606/50 |
| 4,483,338 A | * | 11/1984 | Bloom et al. | 606/50 |
| 4,548,207 A | * | 10/1985 | Reimels | 606/50 |
| 4,674,499 A | | 6/1987 | Pao | |
| 4,800,878 A | * | 1/1989 | Cartmell | 606/45 |
| 5,089,002 A | * | 2/1992 | Kirwan, Jr. | 606/50 |
| 5,814,043 A | * | 9/1998 | Shapeton | 606/48 |
| 5,925,045 A | | 7/1999 | Reimels et al. | |
| 5,972,416 A | | 10/1999 | Reimels et al. | |
| 6,174,310 B1 | | 1/2001 | Kirwan, Jr. | |
| 6,676,660 B2 | | 1/2004 | Wampler et al. | |
| 2007/0032789 A1 | * | 2/2007 | Gonnering et al. | 606/42 |
| 2008/0004619 A1 | * | 1/2008 | Malis et al. | 606/42 |

\* cited by examiner

*Primary Examiner* — Joseph Stoklosa
*Assistant Examiner* — Jocelyn D Ram
(74) *Attorney, Agent, or Firm* — Allen, Dyer, Doppelt, Milbrath & Gilchrist, P.A.

(57) ABSTRACT

A bipolar electrosurgical coagulator utilizes a handle having distal and proximal ends with a conductor carried by the handle and having coaxial inner and outer electrically conductive elements. The conductor extends from the distal end of the handle to a coagulating tip, with the proximal end of the conductor secured within the handle for electrical interconnection with a power source entering the handle at its proximal end.

26 Claims, 11 Drawing Sheets

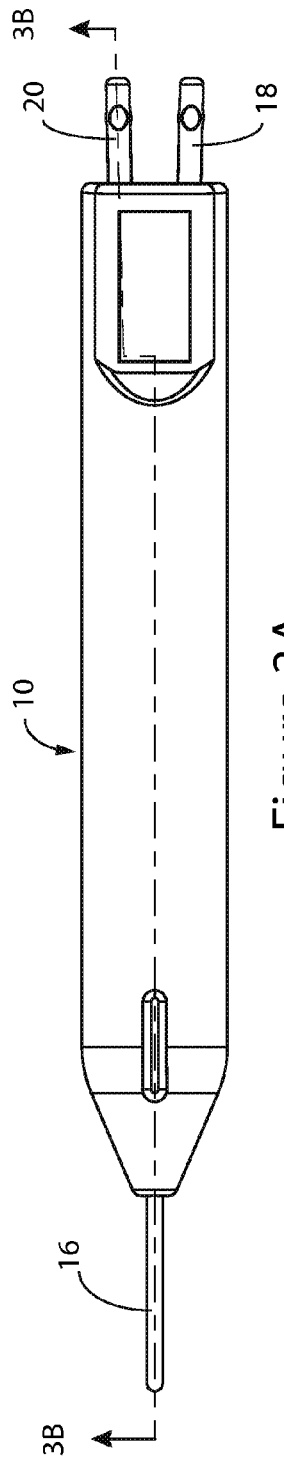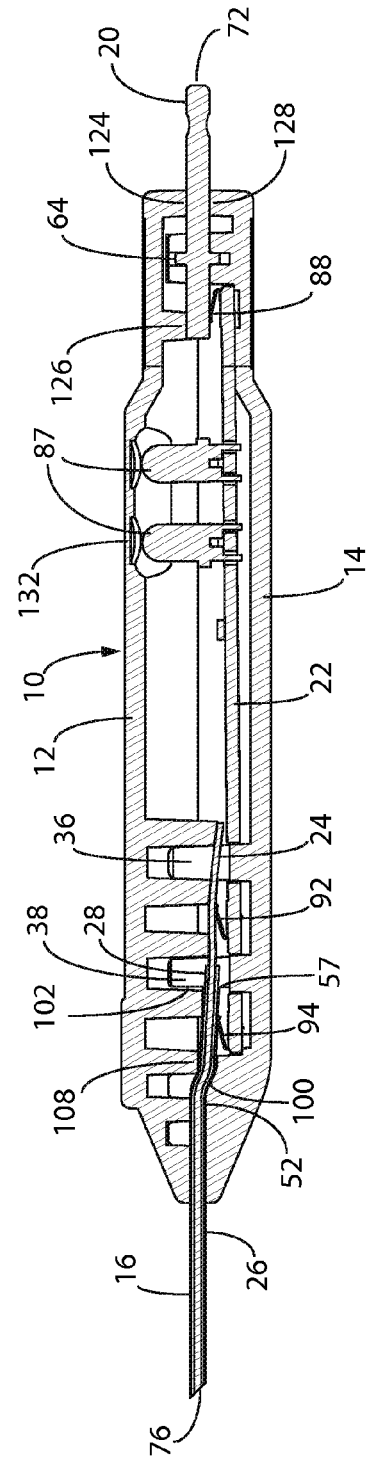
Figure 3A
Figure 3B

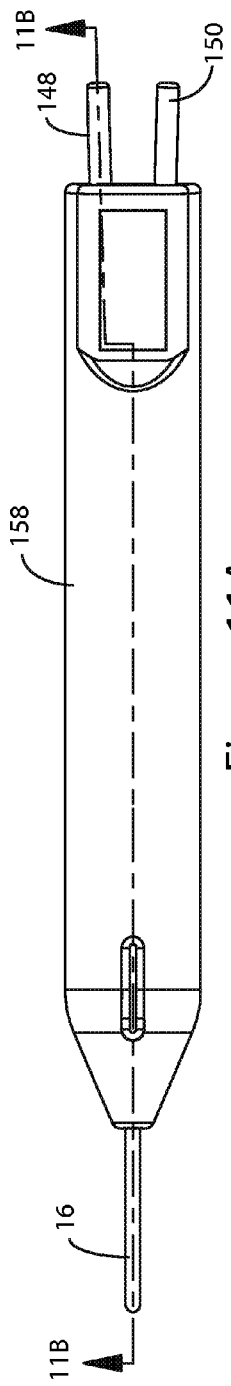
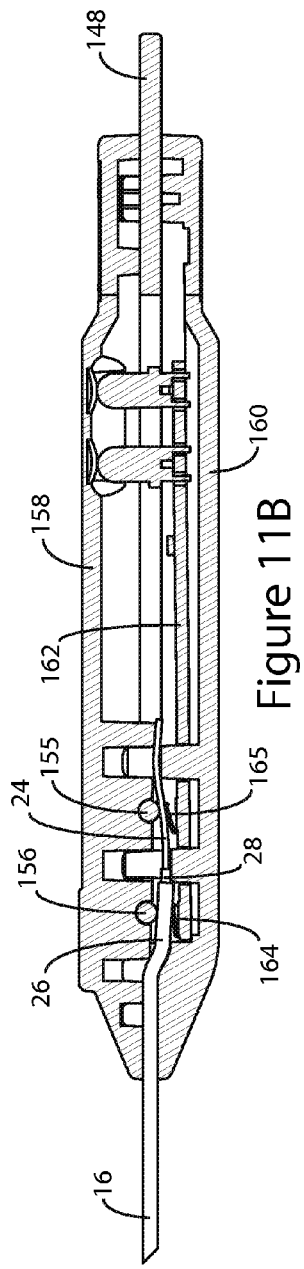
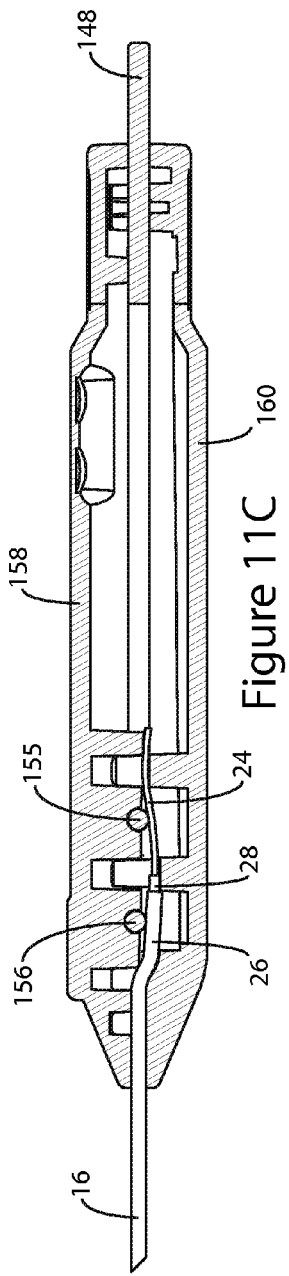

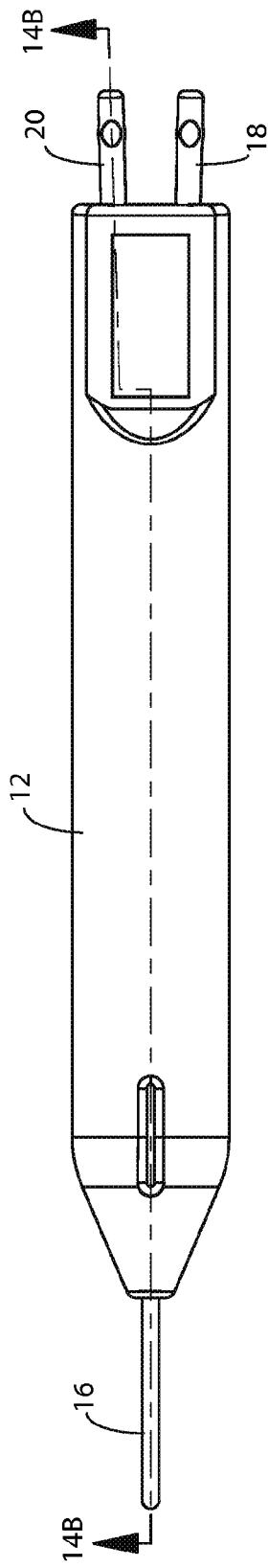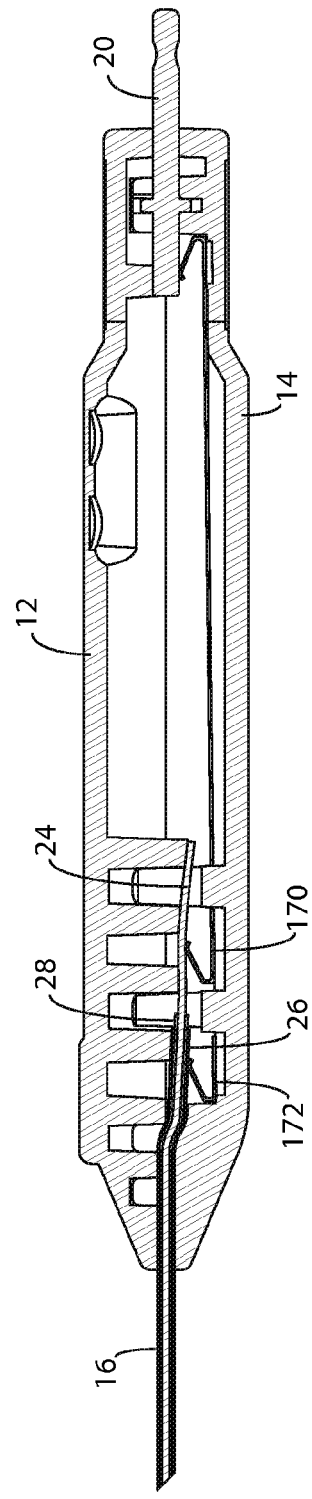
Figure 14A
Figure 14B

BIPOLAR ELECTROSURGICAL COAGULATOR

CROSS REFERENCE TO RELATED APPLICATION

This application claims priority to provisional application Ser. No. 61/240,862, filed Sep. 9, 2009.

BACKGROUND OF THE INVENTION

The application of high frequency electrical energy for coagulation is common in many surgical procedures. Coaxial bipolar coagulators are often used in surgical procedures such as ophthalmic procedures where discrete application of coagulation energy is required to stop bleeding. The term "bipolar" is used when describing a coagulator that has two separate conductive paths (also referred to as poles or electrodes) contained within the device, where one pole can act as the current source and the other as the electrical return or ground. In contrast, a monopolar device contains one conductive pole, such as the current supply, and the other pole or ground electrode is external to the device.

Disposable coaxial bipolar coagulators are handheld devices that have an electrical connector at the proximal end of the instrument and a slender coaxial bipolar probe tip at distal end. The electrical connector consists of two protruding pins for connection to a bipolar electrosurgical generator console which supplies the high frequency coagulating current. The coaxial bipolar tip is a slender probe consisting of two conductive poles electrically isolated from one another where the ends of both terminate in close proximity to one another at the distal end of the probe tip. The probe tip is constructed of two conductors in a coaxial relation where the one resides inside the other and the two are isolated by a concentrically disposed dielectric such as plastic. The outer conductor is often a stainless steel tube and the inner is often a stainless steel wire coated with a plastic dielectric. In use, contact of the distal tip poles with tissues and fluids enables the conduction of high frequency current between the tip poles and through the surrounding tissues and fluids for localized coagulation.

Poor coagulation performance, from insufficient power delivery as well as non-functioning units, typically from bad electrical connection or short circuit, are common deficiencies of existing coaxial bipolar coagulator devices and a frequent source of complaint from end users.

A common difficulty with bipolar coaxial coagulators has been to electrically connect the coaxial inner and outer conductors of the tip with the electrical connector at the proximal end of the device. Historically, these devices include an electrical assembly in which the inner and outer conductive electrodes of the coaxial bipolar tip are each coupled one to each of the electrical connector pins that form the two pin connector. Sometimes one or both the inner and outer coaxial tip electrodes are connected directly one to each of the connector pins, and sometimes one or both of the tip electrodes are connected indirectly one to each of the pins using an intermediate conductive element such as a wire. Whether one of the tip electrodes is fastened directly to one of the connector pins, requiring at least one connection or indirectly, requiring two or more connections, all of these connections are made by use of mechanical fastening methods such as welding, soldering, and/or crimp connection. An example of a crimp connection is when one or more conductive elements, such as a wire, are placed inside a channel, sleeve or other opening in a malleable conductive component. The opening is then squeezed closed securing the wire in the opening.

In fastening the conductive elements together, an electrical assembly is made in which the inner and outer conductors of the coaxial probe tip are mechanically attached to the connector pins. This electrical assembly is then retained within a plastic handle in either of two manners. One method is to place the assembly into a premolded handle consisting of two or more pieces which is then secured around the assembly by such methods as gluing, press-fit or ultrasonic welding.

Another method is to over-mold the electrical assembly to create the device handle. In the process of over-molding, the electrical assembly is placed into a mold tool where the portion of the assembly to be over-molded with the plastic handle resides inside the mold cavity, and the components which will protrude from the device handle, such as the tip and connector pins, project outside the cavity. The handle is then formed around the electrical assembly by injection of plastic (typically thermoplastic). Once the plastic is cooled and solidified, the unit is removed from the mold and the device assembly with an over-molded handle is complete.

A common problem with the assembly methods described above is that if one of the mechanically fastened components or if one of the connections breaks or fails due to stress or fatigue, the circuit can become open and the device will not function.

In the case of over-molding the device handle, the process of encapsulation and shrinkage of the polymer as it cools assists in secure retention of components contained within and protruding from the molded handle. However, a side effect from the over-molding technique is that the stresses from the over-molding process, including polymer injection and plastic shrinkage as it cools from elevated temperatures, can induce sufficient stress and tension on the components and connections that can ultimately lead to breakage and electrical failure of the device, if not immediately following molding, then sometime in the future. As a result, the over-molded components and connections forming the electrical assembly need to be sufficiently strong and secure to avoid subsequent electrical failure.

In the case of the electrical assembly being placed into a pre-molded handle, the high stresses from polymer injection and material shrinkage from cooling found during insert molding are not present as the handle is molded prior to assembly. However, the electrical assembly and protruding components are also not as inherently secure within the handle. Therefore, greater attention must be paid to securing components (particularly protruding functional components) to prevent or limit their movement as well as prevent unwanted stress on components and connections that could lead to device failure. An additional problem can arise once the components are secured within the pre-molded handle. The sterilization of surgical devices often requires exposure to an elevated temperature. If the electrical assembly is sufficiently retained within the pre-molded handle, thermal expansion of the polymer handle can result in damaging stresses to the electrical assembly components and connections similar to those which can occur during over molding.

A common drawback with the above-described methods of manufacture is the relatively costly and laborious additional process of mechanically fastening the electrical connections between the components that comprise the coaxial tip conductors, pin connectors and intermediate circuit elements, if applicable, that form the device's electrical circuit assembly prior to incorporation into the device handle, for without doing so, the conductive integrity between these components within the finished device is not assured.

Another problem with coaxial bipolar coagulators manufactured by the methods described above is that of axial migration or movement of one or more of the coaxial tip elements which can cause unwanted misalignment of the distal tip geometry. Thermal expansion and contraction of the device handle can place stresses on the components and connections within the device as described above. In addition to causing mechanical failure of these components and connections, these stresses can also cause the inner and outer conductive elements of the coaxial tip to shift axially against one another causing an unwanted misalignment of the distal tip profile, such as a retraction of the inner conductive pole which can reduce tissue contact and diminish coagulation performance.

Coagulation performance is important to surgeons. This is particularly the case for eye surgeons as there is often need to quickly stop unwanted bleeding before it obscures visibility, as well as to coagulate thoroughly so as to prevent unwanted post operative bleeding. New ophthalmic surgical techniques utilizing smaller incisions have created the need for bipolar coaxial coagulators with increasingly smaller tip diameters. As the coaxial tip becomes smaller in diameter, the ability of the device to deliver coagulation power is diminished, and it is therefore increasingly difficult to provide sufficient coagulation power to thoroughly address unwanted bleeding. A further complication of the variation in power delivery between different tip designs occurs frequently when two bipolar coagulators of sufficiently differing tip diameter are used in back-to-back cases or as often happens are used in the same case. Because these units often require significantly different power settings to achieve the desired coagulation results, it is not just an inconvenience but also a matter of safety that the power setting on the console be adjusted to the correct setting. This is particularly important when the power needs to be adjusted from high to low prior to use to avoid unwanted injury.

What makes a non-functioning, or seemingly non-functioning, bipolar coagulator such a big problem for the surgeon is that it is frequently only discovered when he or she attempts to coagulate tissue with the device during a surgical procedure. Most commercially available bipolar electrosurgical generators have a visible light and/or audible tone on the console to indicate when the power is activated and being supplied to the console output terminals. However, if a handpiece or power cord is improperly connected or if there is a fault in either the handpiece or cord, there is no ready means to verify that power is being applied to the hand unit before attempting to use the device. Therefore, if a bipolar coagulator unit appears to not be working properly, a common occurrence is to then troubleshoot the cause during the surgical procedure in a manner similar to the following: First is to typically check the settings on the generator and verify all electrical connections. If no fault is found there they might then try to turn up the power setting on the generator and the surgeon would try it again. If that does not correct or overcome the problem, then next would be to replace either the power cord and/or the bipolar coagulator handpiece with a new unit in an effort to remedy the fault, and again the surgeon would re-try the coagulator to see if it is functioning. The delay in treatment caused by this type of fault, as well as the procedure to remedy it is something that many eye surgeons know well, and it is more than just an aggravation. It can also become an issue of safety as not only is treatment delayed, but other complications such as impaired visibility may arise.

SUMMARY OF THE INVENTION

The invention described herein addresses the need for a coaxial bipolar coagulator that is very robust and reliable, offers improved coagulation performance, and comprises a means for providing a visible signal to indicate the presence of supplied power within the handpiece, such as an indicator light, and does so in a manner that is cost effective to manufacture.

The preferred embodiment of this invention is a disposable bipolar coaxial coagulator having an insulating handle with a protruding coaxial probe tip comprising an inner conductor insulated by a dielectric plastic concentrically disposed within an outer cylindrical tube conductor where both the inner and outer conductive poles terminate in close proximity to the distal tip. An electrical connector is included at the proximal end of the instrument for connection with a power cable extending from a bipolar electrosurgical generator as the power source.

Further, the device comprises that of a coaxial bipolar coagulator with the assembly of the device handle securing the coaxial tip and connector pins within the device handle by use of mating interlocking profiles and features incorporated into the components and the molded handle. The inner and outer conductive electrodes of the coaxial tip and the connector pins, via direct connection of these circuit elements or through the use of intermediate circuit elements such as a printed circuit, wire or preformed conductors, are secured in electrical contact via spring-loaded compressive force by means of assembly and closure within the device handle, and without the need to mechanically fasten or secure these electrical connections prior to incorporation into the device handle.

Product reliability, safety and performance are improved through the incorporation of the following design features:

In an effort to improve the conductive circuit reliability and significantly reduce the risk of a broken or failed connection or component, the electrical connection of the bipolar tip with the connector pins is accomplished utilizing spring force to hold conductive elements in contact. This is accomplished by either direct spring-loaded contact of the inner and outer conductive poles of the coaxial tip with one each of the connector pin poles, or by indirect contact, whereby the use of an intermediate conductor such as a spring connector or wire is held in spring-loaded contact with one or both poles of the coaxial tip and/or one or both connector pin poles. An example of two conductors in electrical contact via spring force is a conductive coil spring compressed against a conductive surface. An important advantage to the use of a spring contact versus a weld, solder or crimp junction is that the spring contact is forgiving to minor translation and angular displacement of the point of contact where a welded, soldered or crimped joint is not and often breaks. Therefore, in using a spring-loaded point of contact, tensile, compressive, shear or other forces placed on the conductive components and connections within the handle as a result from thermal expansion and contraction of the handle caused by sterilization typically results in a minor translation or angular displacement of the contact point, thus relieving the stress without breakage and without losing electrical contact.

Another important feature of this invention that improves product reliability and robustness is the means by which the protruding coaxial bipolar probe tip is retained within the device handle, utilizing a molded handle design consisting of two mating components that are assembled together. The coaxial tip which protrudes from the distal end of the molded handle is retained within the handle by nesting a non-radial symmetric profile in the proximal region of the coaxial tip, such as one formed by one or more bends in that proximal region. This profile of the coaxial tip then nests within a cavity formed within the molded handle components. When the molded handle components are brought together and secured, by example ultrasonic welding, the bent region of the coaxial tip becomes captive within the mating cavity profile of the two handle components and the coaxial tip is then secured within in the handle against axial, torsional and radial displacement.

The bend profile in the proximal region of the tip serves to act as a feature to secure the tip within the device handle as well as act as a feature to secure the inner conductor and insulation within the outer conductor tube to prevent axial movement or translation of the inner and outer elements so as to prevent unwanted misalignment of the distal probe tip profile.

Another feature that improves the product reliability and robustness is the means by which the protruding pins of the male connector are retained within the handle. The cable connector consists of two pins which protrude from the proximal end of the molded handle. Preferably, each pin is retained within the handle by means of nesting a non-radial symmetric profile formed on the connector pin component, such as one formed by a flange with one or more flats on the flange periphery, with a mating geometry molded within the handle components. The retaining profile of the pin is placed within the nesting cavity in one of the molded handle components. When the two mating molded handle components are brought together and secured by a method such as an ultrasonic weld, the non-radial symmetric profile of the connector pin becomes secured within the mating nesting profiles of the two handle components and the connector pin is then retained within the handle against axial, radial and torsional displacement.

An important additional feature of the preferred embodiment of the invented coaxial bipolar coagulator is the inclusion of an auxiliary resistive circuit set as a bridge circuit across the two poles of the device. One important reason for the inclusion of the auxiliary resistive circuit is to use it as a means to alter the power output of the device. The power output of many electrosurgical generators varies with the resistance (or impedance) of the load placed on the generator. Often the power output of the generator is significantly higher at impedance values less than that which is characteristic of a coaxial bipolar coagulator in use. Therefore, the inclusion of the resistive bridge circuit, which acts as a current divider to a resistive working load (such as bodily tissue and fluid) placed in contact the coaxial tip electrodes, is a means to lower the overall device impedance. Lowering the device impedance is a means by which to potentially increase the power output of the generator by an amount greater than that dissipated by the bridge circuit, and in effect increase the power delivered at the device distal tip, thus improving the device coagulation performance. The inclusion of the resistive bridge circuit can therefore be used as a means to alter the coagulation performance of one device so that the desired coagulation results are achieved at a power setting closer to that of other utilized coagulation devices.

Another important feature of the preferred embodiment is the inclusion of a power indicator light. The inclusion of the light improves device safety by providing a ready means to visibly confirm that the device is connected properly to the generator and that supplied power is present within the coagulator handpiece upon activation of the generator output. One manner to do this is to use a parallel resistive circuit within the device as described above, and to utilize the power shunted by the circuit to power a visible light within the coagulator handpiece to indicate the presence of supplied electrical current.

Another important additional feature of the invented coaxial bipolar coagulator is the inclusion of an intermediate conductive element to connect the poles of the coaxial tip to the connector pin poles. Of particular interest and importance in the preferred embodiment of the coagulator is the inclusion of a printed circuit utilized as a conductive element to facilitate the connection of the inner and outer poles of the coaxial tip to the connector pin poles. The printed circuit also facilitates the incorporation of a parallel bridge circuit which can be used to enhance the device power delivery as well as power a visible indicator light.

DESCRIPTION OF THE DRAWINGS

FIG. 3A is a top plan view of the bipolar coaxial coagulator shown in FIGS. 1A, 1B and 2.

FIG. 3B is a cross-sectional view of the coagulator of this invention, taken along the line 3B-3B in FIG. 3A.

FIG. 11A is a top plan view of the alternate embodiment of a coagulator shown in FIGS. 9 and 10.

FIG. 11B is a cross sectional view of the embodiment shown FIGS. 9, 10 and 11A, taken along the lines 11B-11B in FIG. 11A.

FIG. 11C is a cross-sectional view similar to that of FIG. 11B with the circuit board 162 shown in FIGS. 9, 10 and 11B removed, illustrating another embodiment of the coagulator of the present invention.

FIG. 14A is a top plan view of the alternate embodiment shown in FIGS. 12 and 13.

FIG. 14B is a cross-sectional view of the embodiment shown in FIGS. 12, 13 and 14A, taken along the line 14B-14B in FIG. 14A.

DETAILED DESCRIPTION

Figure 1A:
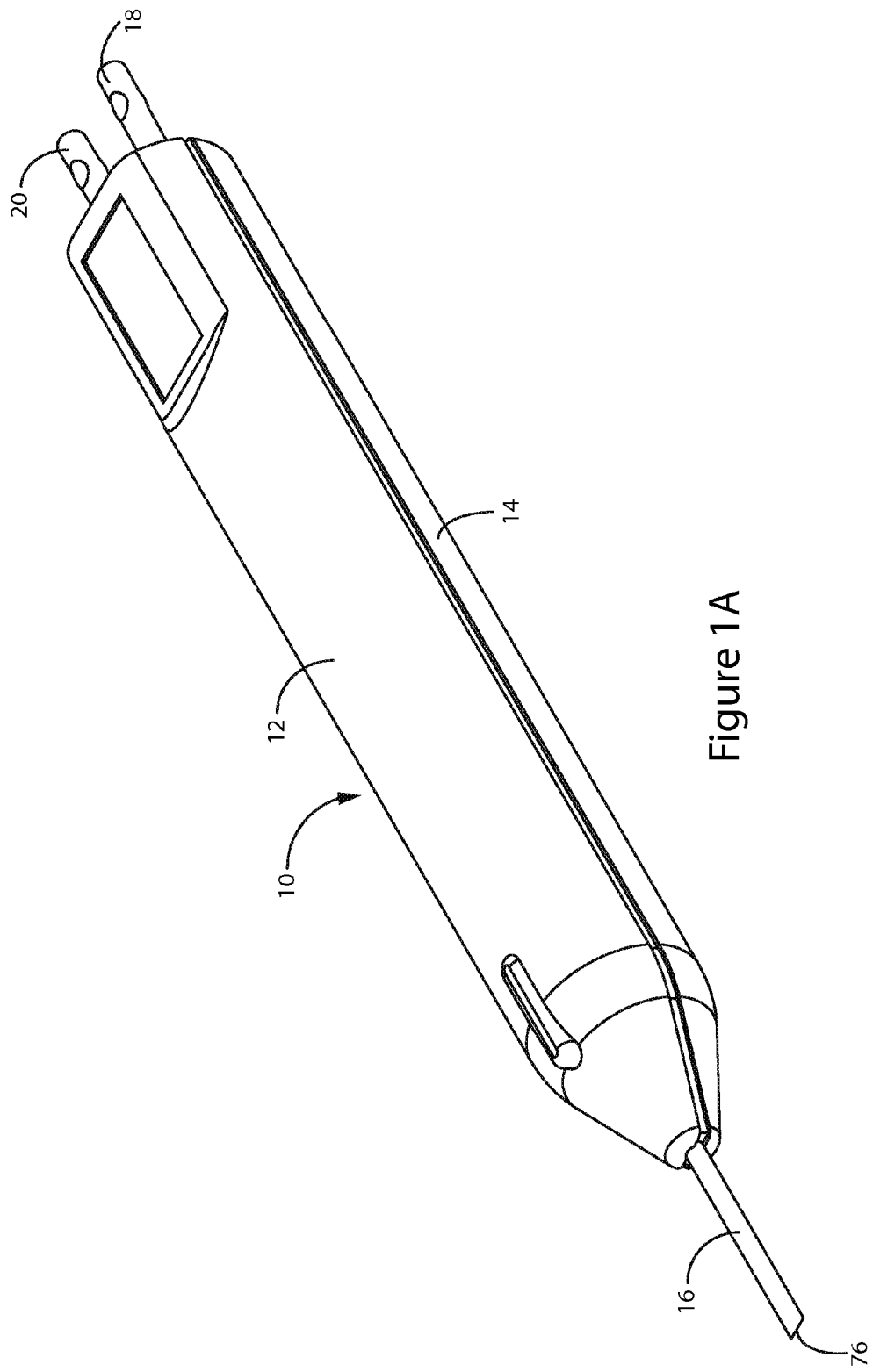
FIG. 1A is a top perspective view of a bipolar coaxial coagulator in accordance with the present invention.
Figure 1B:
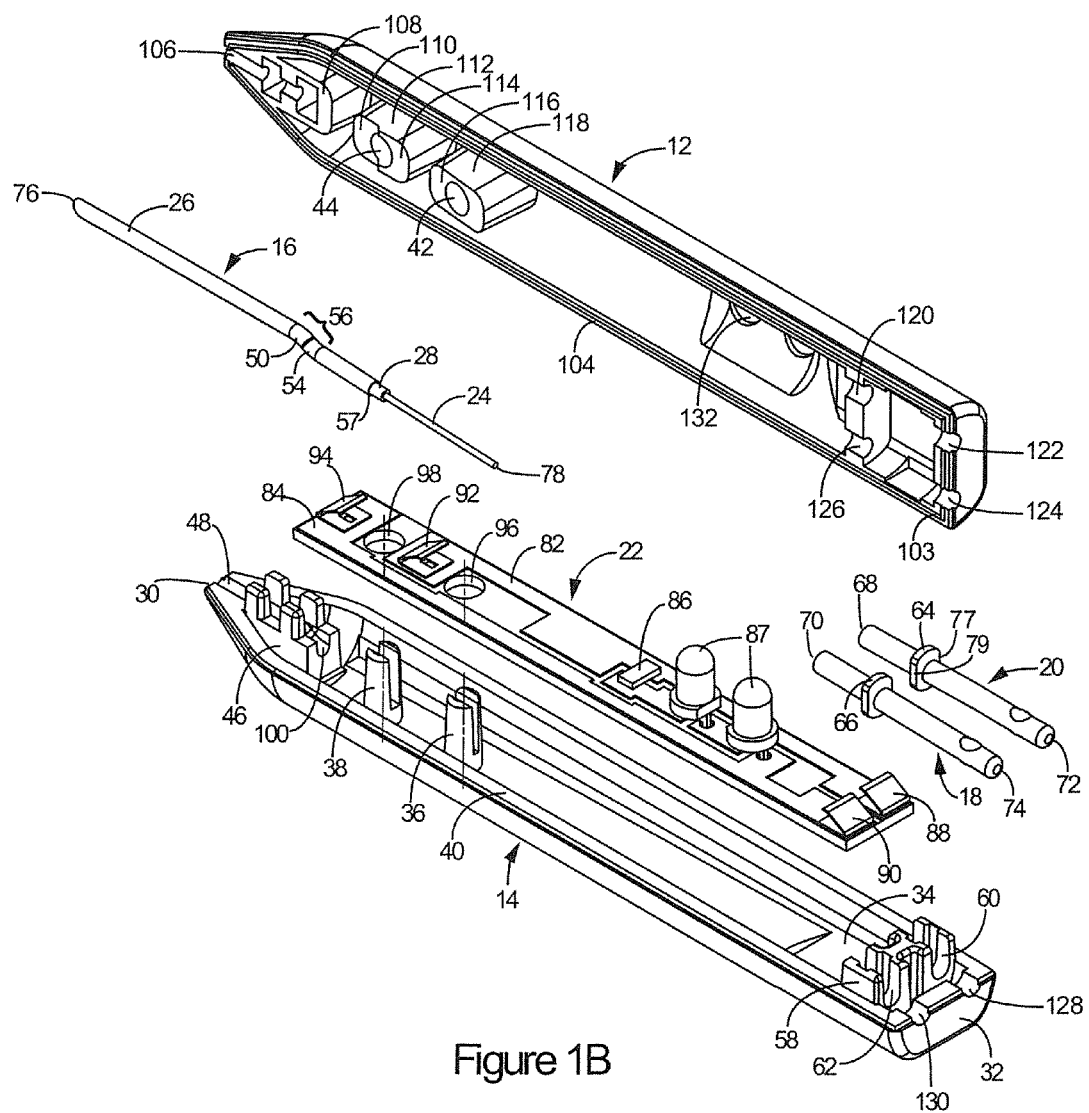
FIG. 1B is an exploded top perspective view of the bipolar coaxial coagulator of FIG. 1A.
Figure 2:
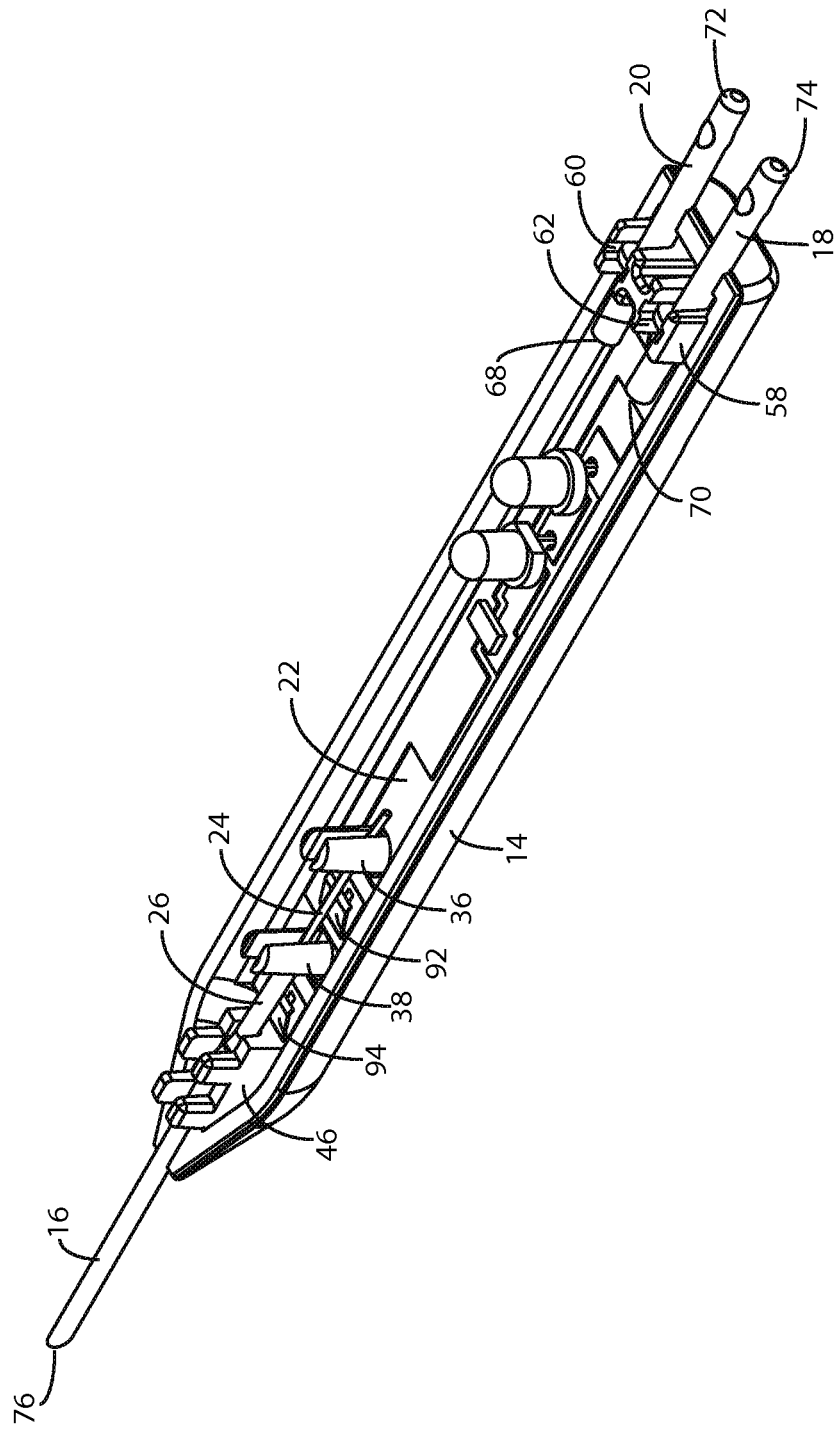
FIG. 2 is a top perspective view of the assembled bipolar coaxial coagulator shown in FIGS. 1A and 1B, with the top plastic handle component 12 removed.

Referring to FIG. 1A: The invented device herein described as a bipolar coaxial coagulator 10. Referring to FIG. 1B: In the preferred embodiment, the bipolar coaxial coagulator consists of top and bottom molded plastic handle components 12 and 14 respectively, a coaxial bipolar distal end or tip 16 consisting of inner conductive element or wire 24 coaxially disposed within a conductive outer tube 26 separated by a circumferential layer of insulation 28 disposed between at least portions of the inner and outer conductors, two electrical connector pins 18 and 20 for connection to a bipolar electrosurgical power supply which is not shown but well known in the art, a printed circuit board 22 as an intermediate conductive circuit element to electrically connect the inner 24 and outer 26 conductive poles of the coaxial tip 16 to the connector pins 18 and 20. In addition to electrically joining the connector pins 18, 20 with the coaxial tip conductive elements 24 and 26, the printed circuit 22 also contains a circuit for indicator lights 87 which are powered and illuminated during delivery of supplied coagulation current from the electrosurgical generator and are visible through the upper semi-translucent device handle 12. The printed circuit 22, coaxial tip 16 and connector pins 18 and 20 nest within handle component 14 forming a bottom handle assembly as shown in FIG. 2. The top mating handle component 12 is then secured down onto the bottom assembly via ultrasonic weld to form the final device assembly. Upon secured closure of the device handle 12 and 14, the coaxial tip 16 and connector pins 18, 20 become secured within the handle assembly axially, radially and torsionally by means of interlocking component features including bends 50 and 54 and flanges 66 and 64 which mate with interlocking cavity and protrusion features within the device molded handle as shown in FIGS. 2 and 3B. In addition to mechanically retaining the coaxial tip 16 and connector pins 18, 20 in place, closure of the top and bottom handle components 12, 14 also secures the electrical connection of the inner and outer coaxial tip elements to the connector pins via compressive force. FIG. 3B shows a sectioned view of the preferred embodiment handle assembly 10 where electrical connection of the coaxial tip inner and outer conductive poles 24, 26 to the connector pins is achieved by means of an intermediary conductor in the form of a printed circuit board 22 which contains a power indicator light circuit. In the later descriptions of alternative embodiments of this invention, configurations are described in which no intermediate conductor is necessary to electrically connect the coaxial tip to the connector pins, alternative intermediate conductor configurations are also discussed, as well as description of an alternate embodiment where the indicator lamp circuit is configured as an optional separate auxiliary circuit and is not an integral part of the bipolar conductive circuit.

Referring to FIG. 1B, the top and bottom handle components 12 and 14 are injection molded from thermoplastic. The bottom handle component 14 has a semi cylindrical outer shape. The distal end of the handle 30 tapers to a slender profile with a semicircular opening 48 where the coaxial tip 16 exits the housing. The proximal end 32 of the handle possesses two semicircular openings 128 and 130 where the two electrical connection pins 18 and 20 exit the housing. Within the central cavity of the bottom handle there is a rectangular cavity 34 with a flat landing area around much of the perimeter of the rectangular cavity 34. This cavity is designed to accept, support and locate the printed circuit board within the bottom handle component 14. Boss protrusions 36 and 38 extend from the bottom inner cavity to substantially above the mating surface 40 of the bottom handle 14. These bosses 36 and 38 serve to locate the flexible stainless steel inner conductor wire 24 of the coaxial tip 16 which passes through the central cavity in these bosses as seen in FIG. 2.

Again referring to FIG. 1B, bosses 36 and 38 mate with circular cavities 42 and 44 in the handle top component 12 to help align the top and bottom handle components for assembly. Within the distal end of the bottom molded handle component 14 there is an internal boss 46 with a contoured cavity 48 designed to accept and closely cradle the underside of the coaxial tip 16 in such a manner where the longitudinal central axis of the straight portion of the coaxial tip 16 distal to bend 50 is coincident with the central axis of the semi-cylindrical cavity profile up to point 52 in FIG. 3B of the sectioned handle assembly.

Figure 4A:
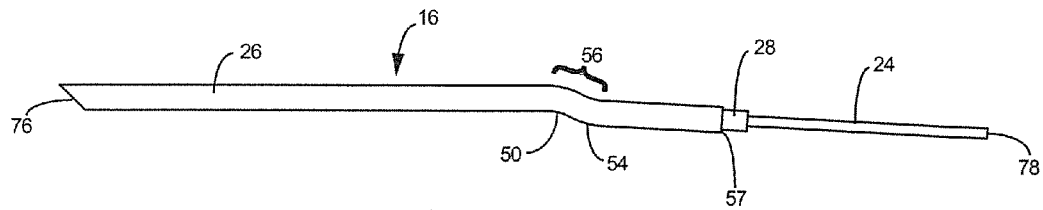
FIG. 4A is a side view of the coaxial probe portion 16 of the coagulator shown in FIG. 1B.

Proximal to point 52 in the molded handle cavity, reference FIG. 4A, the offset in area 56 in the coaxial tip 16 formed by bends 50 and 54 is nested, reference FIG. 3B, in a similarly shaped profile in the cavity where an allowance is made for the offset in the coaxial tip to project downward into the handle cavity as shown within molded boss 46 in FIG. 2. Referencing FIG. 1B, at the proximal end 32 of the bottom molded handle 14 there is a boss 58 with two laterally adjacent cavities 60 and 62 designed to receive connector pins 18 and 20 in such a way that flange 64 is nested within the boss cavity 60 and flange 66 within cavity 62 with the flats on the flanges dispositioned laterally as shown. Therefore permitting end 68 of pin 20 and end 70 of pin 18 to project into the handle cavity for internal electrical contact as well as permitting ends 72 and 74 to protrude axially from the proximal housing end 32 for external electrical connection.

Figure 4B:
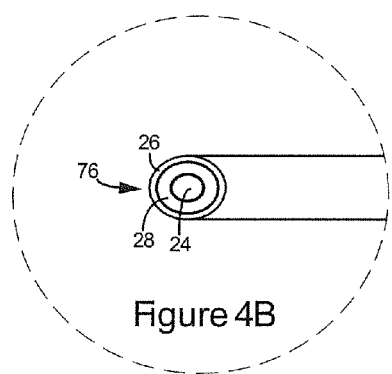
FIG. 4B is an enlarged side view of the tip end 76 of the probe shown in FIG. 4A.

Referencing FIGS. 4A and 4B, the coaxial bipolar distal tip assembly 16 consists of an outer tube conductor 26, an inner wire conductor 24, and an electrical insulating layer 28, disposed between the inner and outer conductors along a substantial portion of the length. Both inner and outer poles terminate at the distal most probe tip 76 in substantially close proximity to one another, see tip FIG. 4B, and at the proximal end 78 which is disposed inside the device handle, the internal conductor 24 projects substantially from the outer conductor 26 enabling adequate room for isolated electrical connection of the inner conductor from the outer conductor. Offset 56 formed by bends 50 and 54 permits adequate axial retention strength so as to prevent movement of the inner conductor and insulative layer within the outer conductor.

The offset 56 also interlocks the coaxial tip assembly into the device handle when handle top and bottom 12, 14 are assembled greatly improving the axial and torsional holding strength of the coaxial tip 16 within the handle. Varying the location, length, and angle(s) of the offset 56 also provides a means to dispose the proximal end of the coaxial tip assembly 16 at the proper location and inclination as required for contact with subsequent internal conductive elements. A note regarding the choice of the bend radius or radii in forming a bend in the coaxial tube; if the radius is too small, it can damage the insulator separating the inner and outer conductors and if the radius is too large it will not adequately secure the inner wire and insulator within the outer conductor. The tubing diameter must also be sufficiently maintained through the bend so as not to damage the insulation material between the inner and outer poles in a manner that could potentially cause an electrical short circuit.

Figure 5:
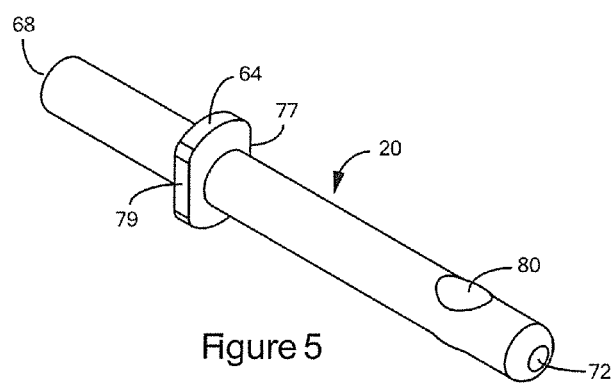
FIG. 5 is a perspective view of the electrical connector pin 20 shown in FIG. 1B.

Referencing FIG. 1B, in the preferred embodiment both electrical connector pins 18, are equivalent in form and are interchangeable. Referencing FIG. 5, each electrical connector pin 20 is manufactured from a single piece of stainless steel and a straight cylindrical shape with a centrally disposed flange 64. The flange provides adequate axial retention strength when nested within the interlocking molded handle cavity 60 during assembly as shown in FIG. 2. Referencing FIG. 5, the flange 64 profile is non-radial symmetric with flat areas 77 and 79. This flange profile enables orientation and prevents rotation of each connector pin 20 about its longitudinal axis when the flange 64 is nested within the mating non-radial symmetric cavity profile within the bottom molded handle cavity. This feature is useful when a pin indentation 80 is added to the protruding portion of the connector pin where axial rotation of the connector pin can result in unsightly misalignment of the indentations in adjacent connector pins.

Figure 6A:
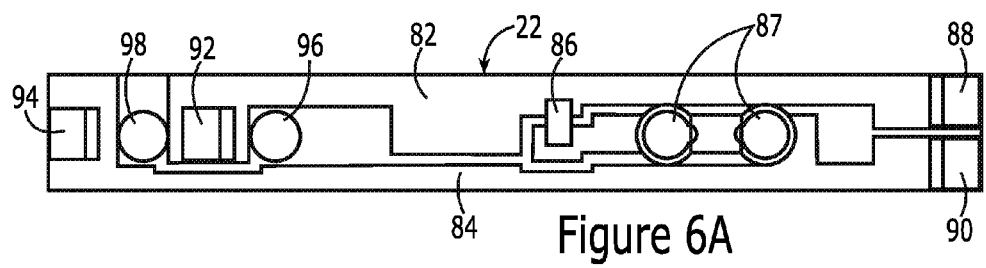
FIGS. 6A and 6B are, respectively, top plan and side views of a printed circuit board 22, shown in FIG. 1B, that is useful with the coagulator of the present invention.
Figure 6B:
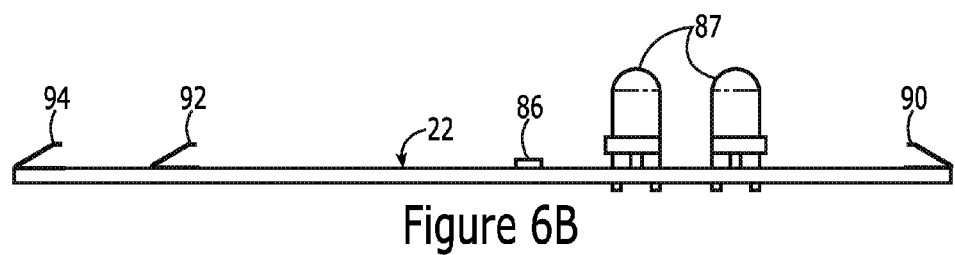
Figure 8A:
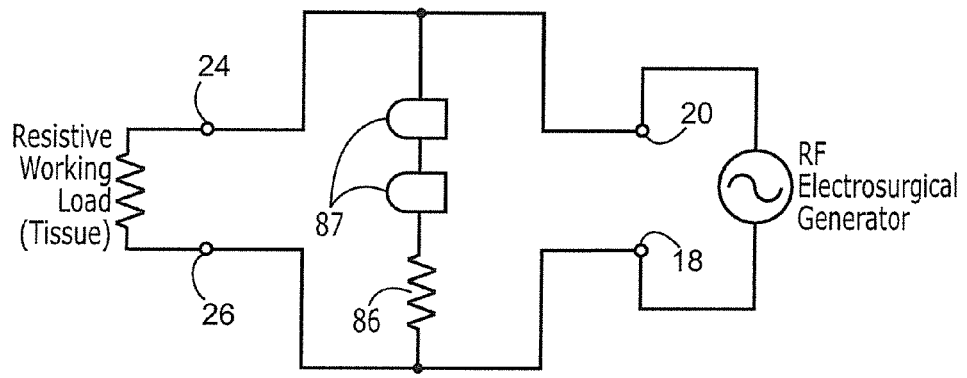
FIGS. 8A, 8B and 8C are different embodiments of circuit configurations useful with the coagulator of the present invention.

Referencing FIGS. 6A and B, in the preferred embodiment, the printed circuit board 22 consists of standard glass/epoxy substrate material and utilizes copper electrical conductive traces and is manufactured in a manner well known in the art. The circuit diagram including the preferred indicator lamp circuit configuration is depicted in FIG. 8A. Referencing FIG. 6A, the layout of the printed circuit includes two main conductive traces 82 and 84 that run lengthwise along the board to connect the two poles of the coaxial tip 16 with the two connector pins 18, 20.

The indicator light bridge circuit connected to traces 82 and 84 and wired in parallel to the tip 16 in identical configuration to that shown in FIG. 8A in that the bridge circuit consists of the resistor 86, and two LEDs 87 wired in series. It is also noted that the LEDs are arranged in opposite polarity (anode to anode) in the preferred embodiment shown in FIG. 8A. In this configuration the LEDs will illuminate in the presence of sufficient supplied radiofrequency (RF) alternating current for coagulation as there is then sufficient energy to back feed the opposing diode. One main advantage to this arrangement is found during inspection of the device to test for electrical isolation of the two conductive poles as well as continuity of the conductive circuit following assembly. Because the LEDs are in opposite polarity, low voltage DC current from an Ohm meter will not conduct through the parallel lamp circuit in either direction. Therefore, the presence of the lamp circuit does not interfere with an open circuit test for isolation and the closed circuit test for continuity.

When the coagulator 10 is connected to a bipolar electrosurgical power supply and the supply is activated, the LEDs illuminate to confirm the presence of supplied electrical current. The resistance of the light circuit is sufficient so as to provide adequate current flow to illuminate the LEDs 87 while preventing excessive current flow that could cause the LEDs to fail prematurely or could adversely impact the device coagulation performance.

Figure 8B:
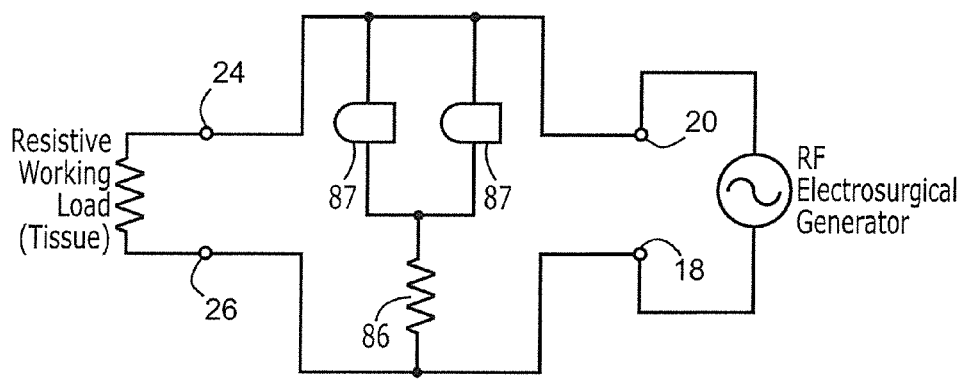
Figure 8C:
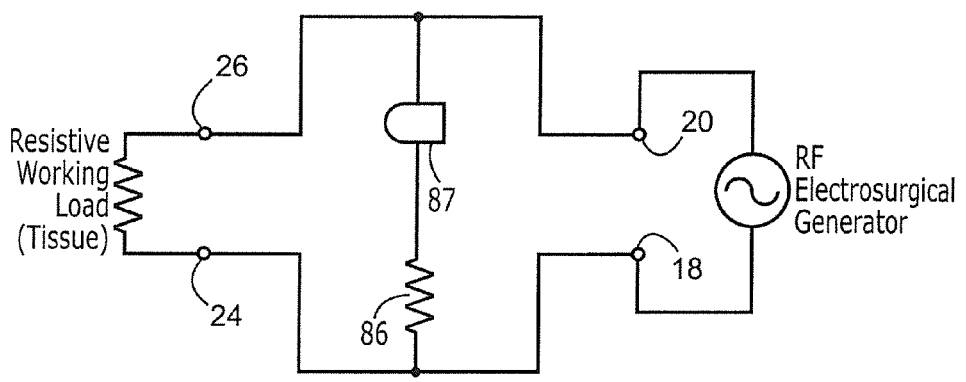

Alternative light circuit configurations are shown in FIGS. 8B and 8C, where in FIG. 8B the resistor is connected to two LEDs wired in parallel and in opposite polarity, and in FIG. 8C the circuit comprises only one LED and one resistor in series.

It is noted that there are several varieties of miniature lamps and LEDs with varying electrical and illumination characteristics and a variety of ways to power them via the supplied RF current. What is shown in the preferred embodiment in FIG. 8A is a circuit which provides adequate visual illumination across a broad range of supplied RF currents.

Figure 7A:
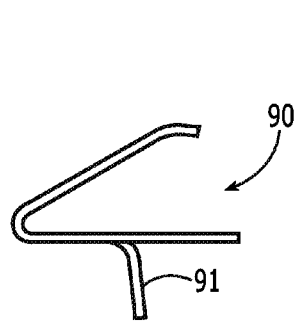
FIGS. 7A and 7B are, respectively, side and perspective views of spring contact 90, shown in FIGS. 1B, 6A and 6B, that is useful with the coagulator design of the present invention.
Figure 7B:
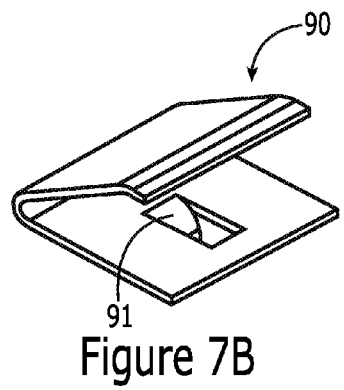

The circuit board 22 shown in FIG. 6A is populated with four conductive spring connectors 88, 90, 92, and 94 preferably stamped from nickel plated spring tempered steel of the configuration shown in FIGS. 7A and B. One spring is positioned at each end of the two main conductive board traces (82 and 84 in FIGS. 6A and B). The springs permit a sufficient amount of compression and accommodation to maintain good electrical contact with two connector pins 18, 20 as well as with the inner and outer electrodes of the coaxial tip 24, 26 during handle assembly as is shown by the placement and perceivable compression of the spring contacts in the Section view in FIG. 3B. Referencing FIGS. 7A and B, each spring connector possesses a central tab 91 which penetrates a through hole in the circuit board 22. The tab 91 assists in locating the spring 90 on the board, as well it facilitates soldering and increases the retention strength of the spring on the board. There are also two clearance holes in the board 96 and 98 in the board 22 which permit the bottom molded handle bosses (36 and 38, FIG. 1B) to pass through the board when it is nested inside the rectangular cavity as shown in FIG. 2.

Assembly of the preferred embodiment of the invented bipolar coagulator 10 is as follows. Referencing FIGS. 1B and 2, first the circuit board 22 is placed inside the rectangular cavity 34 of the bottom molded handle 14 in the orientation shown. Next, connector pins 18 and 20 are placed one each into the laterally adjacent cavities 60 and 62 at the proximal end of the handle such that the respective flange area is nested within the mating cavity within the boss, and in such manner that the longer external connector ends 74 and 72 of the connector pins are protruding out of the proximal end of the handle. The internal ends 70 and 68 of the connector pins are disposed internally, and reside vertically above the spring connectors 90 and 88 on the circuit board. The non-radial symmetric profile of the flange on the connector pins only permits it to be placed into the boss with the flat profiles oriented laterally.

The coaxial tip 16 is then placed within the mating cavity at the distal end of the bottom molded handle in such a manner that offset 56 formed by bends 50 and 54 is displaced downwardly into the mating tip cavity and in such a manner that the underside of offset 56 of the coaxial tip is nested in close alignment with mating cavity feature 100 of FIG. 3B. In further, end 57 of the outer conductor of the coaxial tip 16 is disposed just distal to face 102 of boss 38 of the bottom molded handle. When the coaxial tip 16 is placed within the bottom molded handle, the region of the external conductive element distal to end 57 but proximal to bend 54 resides directly above spring contact 94 of the circuit board. The internal conductive element 24 of the coaxial tip is disposed within the central cavity of boss 38 and 36 where the region of element 24 between bosses 38 and 36 passes directly over spring contact 92 of the circuit board as shown in FIG. 2.

Referencing FIGS. 1B and 3B, the molded handle top 12 is then placed onto the assembly in such a manner that bosses 38 and 36 of the lower handle seat within mating cavities 44 and 42 of the molded top handle respectively. The top handle 12 is seated fully down onto the bottom handle assembly via a compressive force which holds the handle closed while the top and bottom 12, 14 are ultrasonically welded together. The small sacrificial ridge 103 on the mating surface of the top handle melts and the top and bottom molded handles become permanently fused along the mating surfaces 40 and 104. The top handle semi-cylindrical tip cavity feature 106 mates with the coaxial tip outer conductor 26 and bottom handle cavity feature 48 to secure the coaxial assembly within the distal end of the handle assembly. Boss feature 108 of the top handle holds the offset region 56 of the coaxial tip distally and down into the cavity region 100 of the lower handle. Surface 110 of boss 112 of the top handle holds the proximal extremity of the outer conductor of the coaxial assembly down in compression with electrical spring connector 94 of the circuit board. Surface feature 114 of boss 112 and surface 116 of boss 118 of the top handle 12 hold the inner conductive wire 24 of the coaxial tip down and in contact against the compressed electrical spring connector 92 of the printed circuit board. It is noted that as the spring connectors on the printed circuit are compressed during assembly to maintain an accommodating and robust electrical connection, the elastic material properties of the outer tube conductor and the inner wire conductor are also utilized to advantage as well as they are also displaced vertically in a spring-like manner as shown and add additional accommodation in maintaining robust electrical contact.

With continued reference to FIGS. 1B and 3B, top handle semi-cylindrical proximal cavity features 120, 122, 126 and 124 secure the electrical connector pins within the bottom handle assembly where feature profiles 126 and 120 of the top handle hold the distal end of the connector pins down and compress them against the electrical spring connectors 90 and 88 of the circuit board. Semi-cylindrical features 122 and 124 mate with the electrical connector pins and semi-cylindrical features 130 and 128 to secure the electrical connector pins within the handle. Area 132 of the top handle has a reduced wall thickness situated above the LEDs to provide sufficient clearance for the LED to fit within the handle and to facilitate visible light transmission through the molded translucent plastic handle.

Figure 9:
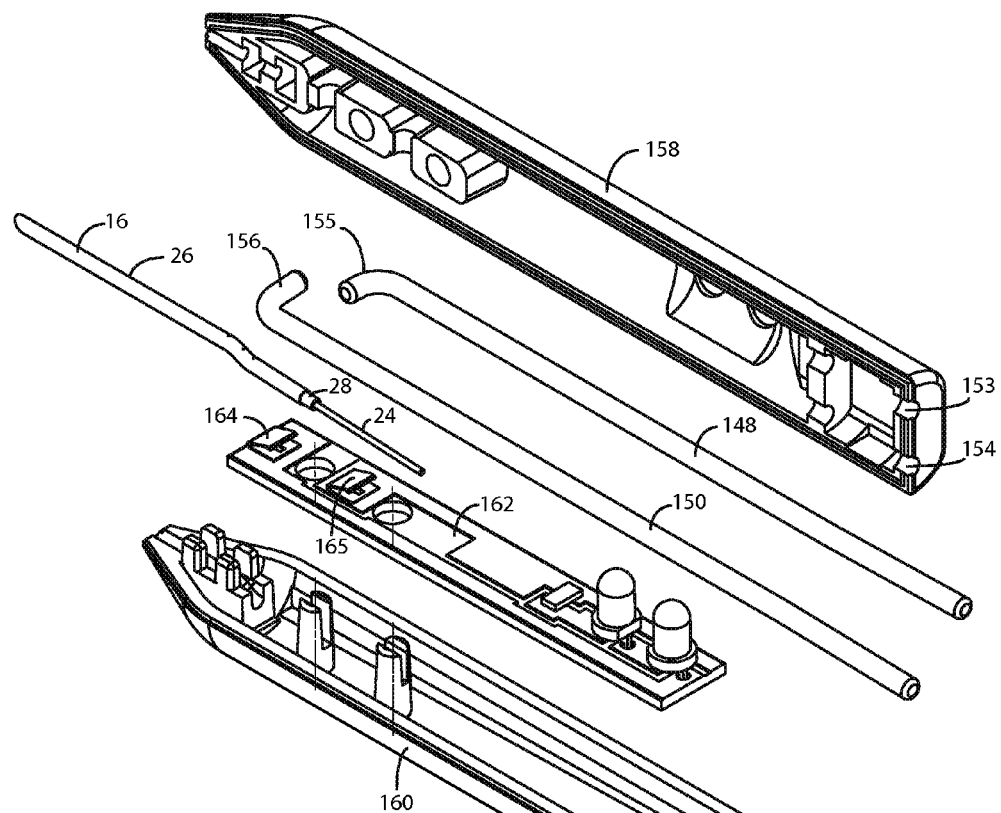
FIG. 9 is an exploded top perspective view of an alternate embodiment of a coagulator in accordance with the present invention.
Figure 10:
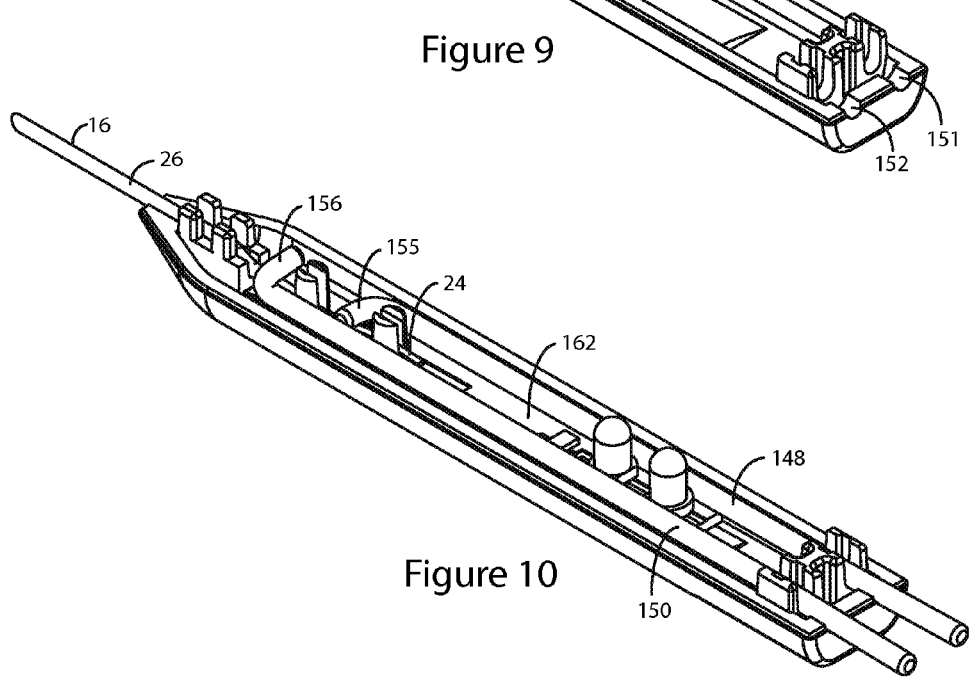
FIG. 10 is a top perspective view of an assembled coagulator in accordance with the embodiment shown in FIG. 9, with the top molded plastic handle component 158 removed.

FIGS. 9 and 10 illustrate another embodiment of the invented bipolar coagulation device wherein the bipolar tip 16 is of a similar design and is secured within the mating handle components in the same manner as discussed in the preferred embodiment. The connector pins 148, 150 extend to the distal end of the device handle where bend profiles 156, 155 rest on top of the coaxial outer tube conductor 26 and the internal conductor wire 24 respectively. Bent profiles 155, 156 in the distal regions of both pins 148, 150 are used to electrically connect the pins to the coaxial tip as well as provide axial and torsional anchorage in addition to the radial anchorage support provided at the proximal location where the connector pins exit the handle housing through the adjoining handle cavities 153 and 152, and 154 and 151.

In addition to illustrating different connector pin designs, FIGS. 9 and 10 also demonstrate that an intermediate conductive member such as a circuit board is not necessary to electrically connect the bipolar tip with the connector pins by means of compressive contact upon placement within and closure of the device handle components 158 and 160. As illustrated in FIG. 11C, both connector pins are electrically connected to the coaxial tip electrodes with no intermediate circuit element. The bent area 155 of connector pin 148 is held in contact with the center electrode 24 of the bipolar tip 16, and bent area 156 of connector pin 150 is held in contact with the outer electrode 26 of the bipolar tip 16.

The difference between section views 11B and 11C is that the printed circuit board 162, referencing FIG. 9, is included in FIG. 11B and is not included in FIG. 11C. Printed circuit board 162 contains the same visible light bridge circuit as the light circuit depicted on the printed circuit in FIG. 8A. However, the board only contains two electrical contacts 164, 165 that connect to the outer and inner poles 26, 24 of the coaxial tip 16. It is interesting to note that the device configuration illustrated in 11B conforms exactly to the circuit diagram in 8A as does the device circuit configuration illustrated in FIG. 3B. In the configuration illustrated in FIG. 11B, however, the circuit board is utilized as a means to incorporate the auxiliary light circuit. A potential advantage to this embodiment is that of having the option to omit the lamp circuit for cost savings when desired.

Figure 12:
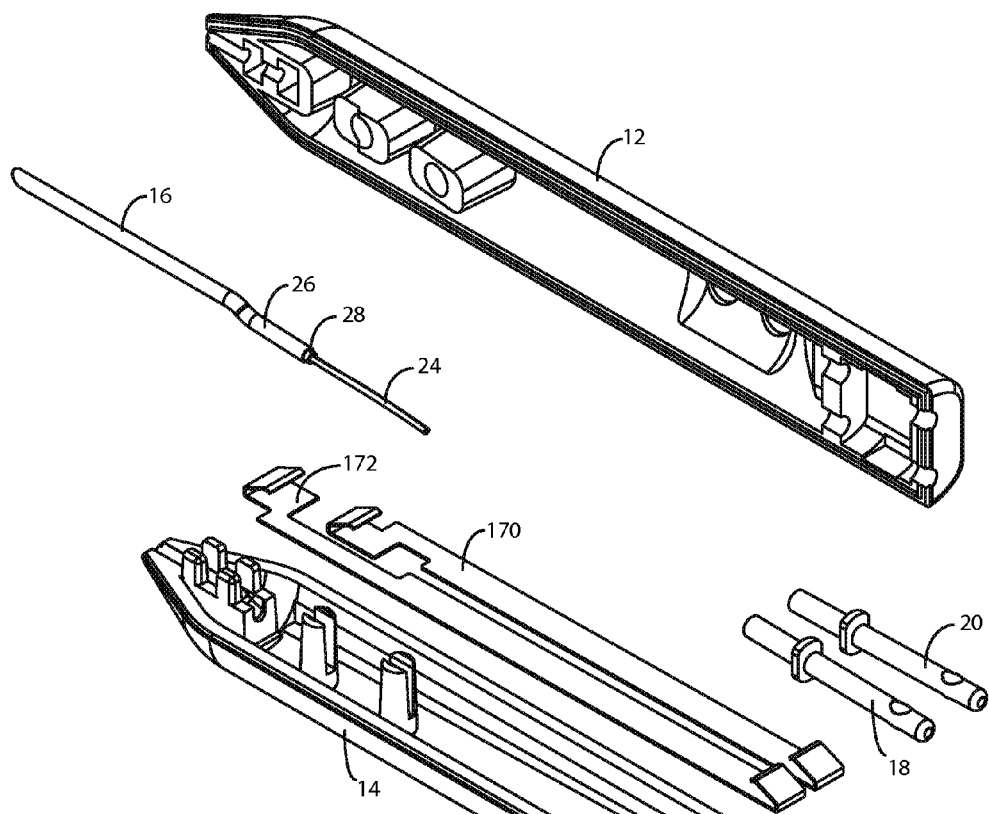
FIG. 12 is an exploded top perspective view of an alternate embodiment of a coagulator in accordance with the present invention.
Figure 13:
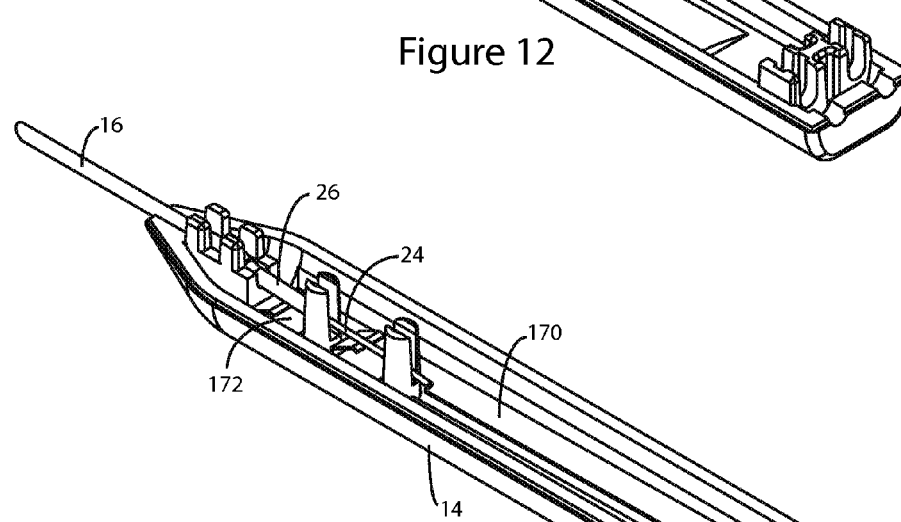
FIG. 13 is a top perspective view of the embodiment shown in FIG. 12, with the top molded plastic handle component 12 removed.

Another embodiment of the invented device includes that of the assembly depicted in FIGS. 12 and 13. In this embodiment the coaxial tip 16 and the connector pins 18, 20 are of a similar design and are secured within the mating handle components 12, 14 in the same manner discussed in the preferred embodiment. However, in this embodiment two metal conductors 170, 172, stamped from nickel plated steel, with incorporated spring connectors are used as intermediate conductive elements to connect the inner and outer poles of the coaxial tip with the connector pins. Thus, the conductors 170, 172 replace the printed circuit 22 utilized in FIG. 1B. As is observed in the section illustration in FIG. 14B, the stamped conductor elements lie within the handle in a sufficiently similar manner to that of the printed circuit with spring connectors in the preferred embodiment shown in FIG. 3B. Referencing FIG. 14B, stamped conductor 172 forms compressive electrical contacts with both the outer electrode 26 of the coaxial tip 16 as well as with the connector pin 18. Stamped conductor 170 forms compressive electrical contacts with both the inner tip electrode 24 and the connector pin 20. One advantage is a potentially lower cost to the preferred embodiment if it were desired to produce a similar bipolar coagulator without a power indicator light. Another method to accomplish removal of the lamp and to potentially reduce cost would be to simply not populate the lamp circuit on the printed circuit board depicted in FIG. 6A. A further note regarding the intermediate conductive elements 170 and 172 in FIG. 12, is that these elements are preformed so as to rest in the largely rectangular space within the handle cavity. An alternate choice of an intermediate conductor could have utilized a flexible preformed or non-preformed conductive wire to replace either or both conductors 170 and 172 provided that sufficient guide features including bosses and/or openings or channels were incorporated within the conductive component and molded handle designs to retain the wire or wires in spring contact with the bipolar tip electrodes 26, 24, as well as the connector pins 18, 20.

It will be appreciated by those skilled in the art that the above-described embodiments are by way of illustration only, and that numerous modifications and changes may be made without departing from the spirit and scope of this invention.

What is claimed:

1. A coagulator useful in surgical procedures, the coagulator comprising:
   a handle formed of an insulating material, the handle having a distal end and a proximal end;
   a conductor carried by the handle, the conductor having coaxial inner and outer electrically conductive elements with an insulating material concentrically disposed between portions of the inner and outer elements, the conductor having a distal region extending from the distal end of the handle and with the inner and outer elements forming a bipolar coagulating probe tip, the conductor further including a proximal region secured within a portion of the handle, the conductor proximal region also being the location for electrical connection of the inner and outer conductive elements to adjoining circuit elements;
   connector means at the proximal end of the handle for interconnection with an electrical power source to permit electrical current to be delivered to the tip of the conductor for coagulation; and means for electrically interconnecting and holding circuit elements by insertion of the circuit elements into the handle.

2. The coagulator recited in claim 1 wherein the conductor comprises at least one bend coincident in both the coaxial inner and outer conductive elements in the proximal region to secure the conductor within the handle against axial and rotational displacement, to secure the inner conductive element against axial displacement within the outer conductor, and to position the proximal region of the conductor for electrical connection.

3. The coagulator recited in claim 1 further comprising at least one bridge circuit within the handle and electrically connected across two poles of the connector means, wherein the bridge circuit shunts a controlled amount of current away from the coagulating probe tip, thus permitting a decrease in the operating electrical impedance as measured between the two poles of the connector means.

4. The coagulator recited in claim 3 wherein the bridge circuit comprises at least one lighting element to produce a visible light when electrical current is supplied to the connector means.

5. The coagulator recited in claim 4 wherein a portion of the handle is translucent and the visible light is visible through the translucent portion.

6. The coagulator recited in claim 1 wherein the connector means comprises two male pins protruding from the proximal end of the handle, wherein at least one pin is secured within the handle against axial and rotational displacement by securing means comprising a non-radial symmetric element protruding from the longitudinal axis of the one pin, to interlock the one pin within the handle.

7. The coagulator recited in claim 6 wherein the non-radial symmetric element comprises a flange on the one pin with at least one flat area on the periphery of the flange.

8. The coagulator recited in claim 1 further comprising a printed circuit within the handle to electrically interconnect at least one of the inner and outer conductive elements to the connector means.

9. The coagulator recited in claim 1 wherein the means for electrically interconnecting and holding circuit elements comprises at least one spring connector.

10. A coagulator useful in surgical procedures, the coagulator comprising:
a handle formed of an insulating material, the handle having a distal end and a proximal end;
a conductor carried by the handle, the conductor having coaxial inner and outer electrically conductive elements with an insulating material concentrically disposed between portions of the inner and outer elements, the conductor having a distal region extending from the distal end of the handle and with the inner and outer elements forming a bipolar coagulating probe tip, the conductor further including a proximal region secured within a portion of the handle, the conductor proximal region also being the location for electrical connection of the inner and outer conductive elements to adjoining circuit elements;
connector means at the proximal end of the handle for interconnection with an electrical power source to permit electrical current to be delivered to the tip of the conductor for coagulation; and wherein
the proximal region of the coaxial conductor is secured within the handle with at least one bend coincident in both the coaxial inner and outer conductive elements in the proximal region to secure the conductor within the handle against axial and rotational displacement, to secure the inner conductive element against axial displacement within the outer conductive element, and to position the proximal region of the conductor for electrical connection.

11. The coagulator recited in claim 10 further comprising at least one bridge circuit within the handle and electrically connected across two poles of the connector means, wherein the bridge circuit shunts a controlled amount of current away from the coagulating probe tip, thus permitting a decrease in the operating electrical impedance as measured between the two poles of the connector means.

12. The coagulator recited in claim 11 wherein the bridge circuit comprises at least one lighting element to produce a visible light when electrical current is supplied to the proximal connector.

13. The coagulator recited in claim 12 wherein a portion of the handle is translucent and the visible light is visible through the translucent portion.

14. The coagulator recited in claim 10 wherein the connector means comprises two male pins protruding from the proximal end of the handle, wherein at least one of the pins is secured within the handle against axial and rotational displacement by a non-radial symmetric element protruding from the longitudinal axis of the one pin, to interlock the one pin within the handle.

15. The coagulator recited in claim 14 wherein the non-radial symmetric element comprises a flange on the one pin with at least one flat area on the periphery of the flange.

16. The coagulator recited in claim 10 further comprising a printed circuit used within the handle as a means to electrically interconnect at least one conductive tip element to a connector element.

17. The coagulator recited in claim 10 further comprising means of electrically interconnecting and holding circuit elements in electrical contact by means of insertion of the circuit elements into the handle.

18. A coagulator useful in surgical procedures, the coagulator comprising:
a handle formed of an insulating material, the handle having a distal end and a proximal end;
a conductor carried by the handle, the conductor having coaxial inner and outer electrically conductive elements with an insulating material concentrically disposed between portions of the inner and outer elements, the conductor having a distal region extending from the distal end of the handle and with the inner and outer elements forming a bipolar coagulating probe tip, the conductor further including a proximal region secured within a portion of the handle, the conductor proximal region also being the location for electrical connection of the inner and outer conductive elements to adjoining circuit elements;
connector means at the proximal end of the handle for interconnection with an electrical power source to permit electrical current to be delivered to the tip of the conductor for coagulation; and
an auxiliary bridge circuit electrically connected across two poles of the proximal connector means, wherein the bridge circuit shunts a controlled amount of current away from the conductor distal tip, thus permitting a decrease in the operating electrical impedance of the device as measured between the two poles of the proximal connector means.

19. The coagulator recited in claim 18 further comprising a means of electrically interconnecting and holding circuit elements in electrical contact by means of insertion of the circuit elements into the handle.

20. The coagulator recited in claim 18 wherein the conductor comprises at least one bend coincident in both the coaxial inner and outer conductive elements in the proximal region to secure the conductor within the handle against axial and rotational displacement, to secure the inner conductive element against axial displacement within the outer conductor, and to position the proximal region of the conductor for electrical connection.

21. The coagulator recited in claim 18 wherein the bridge circuit comprises at least one lighting element to produce a visible light when electrical current is supplied to the connector.

22. The coagulator recited in claim 21 wherein a portion of the handle is translucent and the visible light is visible through the translucent portion.

23. The coagulator recited in claim 18 wherein connector means comprises two male pins protruding from the proximal end of the handle, wherein at least one pin is secured within the handle against axial and rotational displacement by securing means comprising a non-radial symmetric element protruding from the longitudinal axis of the one pin, which is useful in interlocking the one pin within the handle.

24. The coagulator recited in claim 23 wherein the non-radial symmetric element comprises a flange on the one pin with at least one flat area on the periphery of the flange.

25. The coagulator recited in claim 18 wherein the auxiliary bridge circuit incorporates the use of a printed circuit as a conductive element between the connector means and the inner and outer conductive elements.

26. A coagulator useful in surgical procedures, the coagulator comprising:
 a handle formed of an insulating material, the handle having a distal end and a proximal end;
 a conductor carried by the handle, the conductor having coaxial inner and outer electrically conductive elements with an insulating material concentrically disposed between portions of the inner and outer elements, the conductor having a distal region extending to the distal end of the handle and with the inner and outer elements forming a bipolar coagulating probe tip, the conductor further including a proximal region secured within a portion of the handle, the conductor proximal region also being the location for electrical connection of the inner and outer conductive elements to adjoining circuit elements;
 connector means at the proximal end of the handle for interconnection with an electrical power source to permit electrical current to be delivered to the tip of the conductor for coagulation; and wherein
 the proximal region of the coaxial conductor is secured within the handle with at least one bend coincident in both the coaxial inner and outer conductive elements in the proximal region to secure the conductor within the handle against axial and rotational displacement.

\* \* \* \* \*